(12) United States Patent
Chmiel et al.

(10) Patent No.: US 9,150,611 B2
(45) Date of Patent: Oct. 6, 2015

(54) AQUEOUS TRANSFER BUFFER

(71) Applicant: Bio-Rad Laboratories, Inc., Hercules, CA (US)

(72) Inventors: Nikolas Chmiel, Fairfield, CA (US); Cory Panattoni, Winters, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/940,147

(22) Filed: Jul. 11, 2013

(65) Prior Publication Data

US 2014/0014514 A1 Jan. 16, 2014

Related U.S. Application Data

(63) Continuation of application No. 12/709,325, filed on Feb. 19, 2010, now abandoned.

(60) Provisional application No. 61/154,711, filed on Feb. 23, 2009.

(51) Int. Cl.
   *G01N 27/447* (2006.01)
   *C07K 1/26* (2006.01)

(52) U.S. Cl.
   CPC ........................................ *C07K 1/26* (2013.01)

(58) Field of Classification Search
   CPC .............. G01N 27/447–27/44752; C07K 1/26
   USPC ......... 204/450, 456, 463, 464, 600, 606, 614; 435/6, 18; 427/2.11
   See application file for complete search history.

(56) References Cited

U.S. PATENT DOCUMENTS

| | | | |
|---|---|---|---|
| 4,840,714 A * | 6/1989 | Littlehales | .................... 204/464 |
| 4,889,606 A | 12/1989 | Dyson et al. | |
| 5,112,741 A | 5/1992 | Palmer et al. | |
| 6,265,588 B1 | 7/2001 | Mullner et al. | |
| 6,726,821 B1 | 4/2004 | Suzuki | |
| 7,166,441 B2 * | 1/2007 | Nadler et al. | ................... 435/23 |
| 7,223,325 B2 | 5/2007 | Landers et al. | |
| 2003/0022258 A1 | 1/2003 | Pardee | |
| 2003/0203465 A1 * | 10/2003 | O'Donnell | ..................... 435/199 |
| 2005/0000811 A1 | 1/2005 | Luka | |
| 2005/0266519 A1 * | 12/2005 | Mellor et al. | ................ 435/69.1 |
| 2006/0210994 A1 | 9/2006 | Joyce | |
| 2006/0272946 A1 * | 12/2006 | Margalit et al. | ............... 204/614 |
| 2008/0171064 A1 * | 7/2008 | Mizuno | ...................... 424/235.1 |
| 2009/0026079 A1 * | 1/2009 | Margalit et al. | ............... 204/464 |

FOREIGN PATENT DOCUMENTS

| | | |
|---|---|---|
| JP | 2001-159621 | 6/2001 |
| JP | 2002-277438 | 9/2002 |
| JP | 2008-538137 | 10/2008 |
| WO | 2006047417 | 5/2006 |
| WO | 2006091525 | 8/2006 |

OTHER PUBLICATIONS

Schiffler et al., Nucleic Acids Research, 2002, 3192-3201.*
Licor, Technical Note, 2008.*
PCT/US2010/024931, "Extended European Search Report", Jun. 13, 2012.
PCT/US2010/024931, "International Preliminary Report on Patentability".
Schiffler et al., "Nucleic Acids Research", 2002, 3192-3201.

* cited by examiner

*Primary Examiner* — Gurpreet Kaur
(74) *Attorney, Agent, or Firm* — Kilpatrick, Townsend & Stockton LLP

(57) ABSTRACT

The present invention relates to an aqueous transfer buffer that provides superior efficiency in transferring polypeptides of a broad range of molecular weight from a matrix used in electrophoresis to another immobilized surface. Also disclosed are electrophoretic methods and devices in which the aqueous transfer solution of this invention is used.

14 Claims, 3 Drawing Sheets

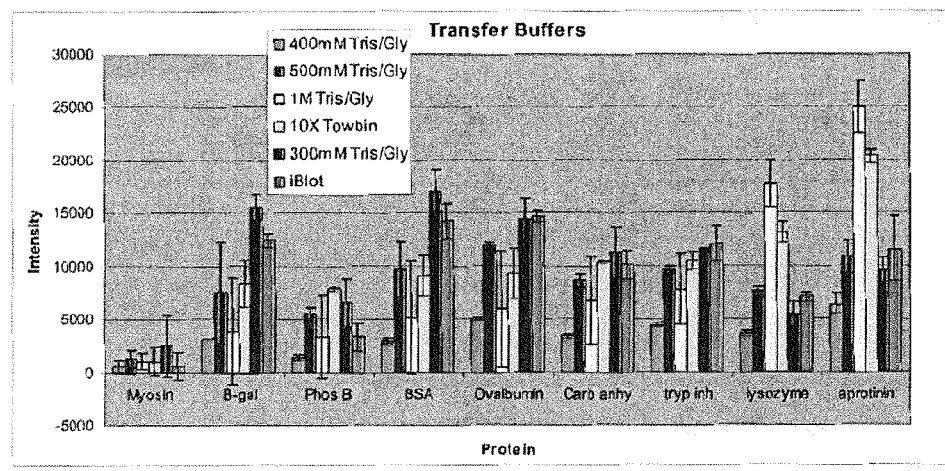
Fig. 2 SYPRO-Ruby signal intensity of SDS-PAGE Broad-Range Standards
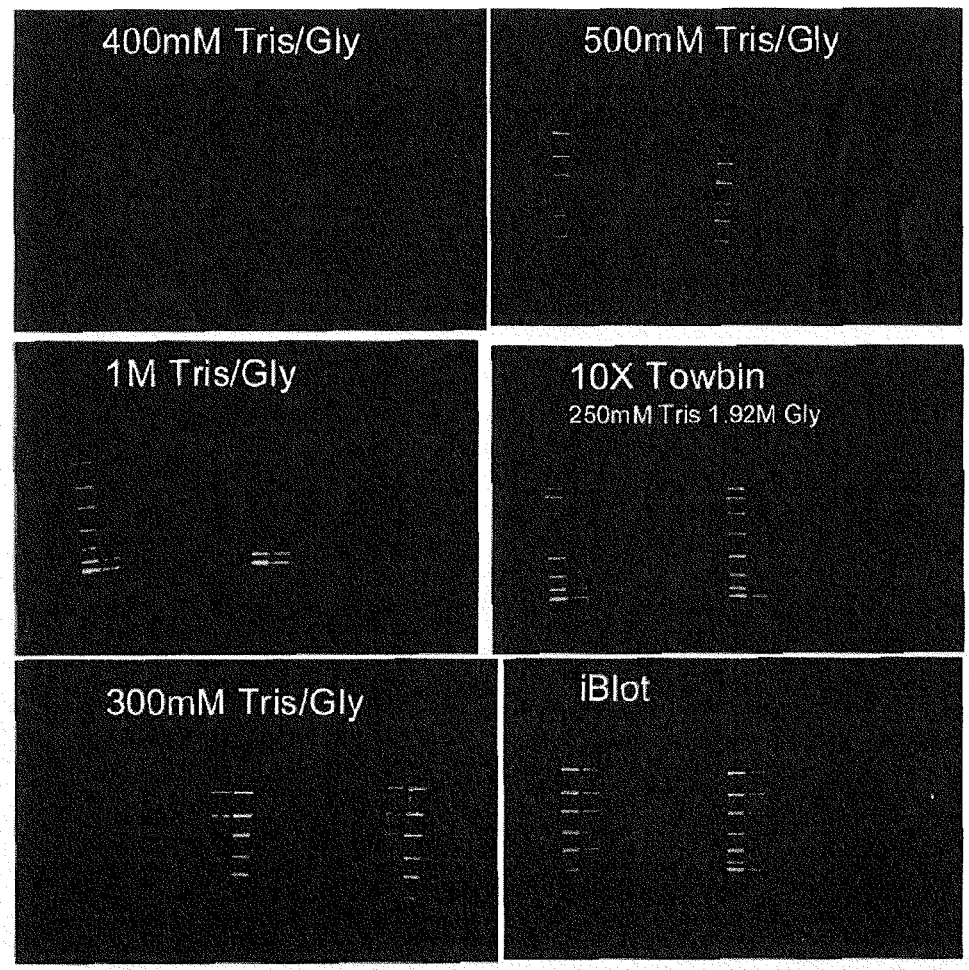
Fig. 3 Blots used for quantitation displayed in Figure 1.

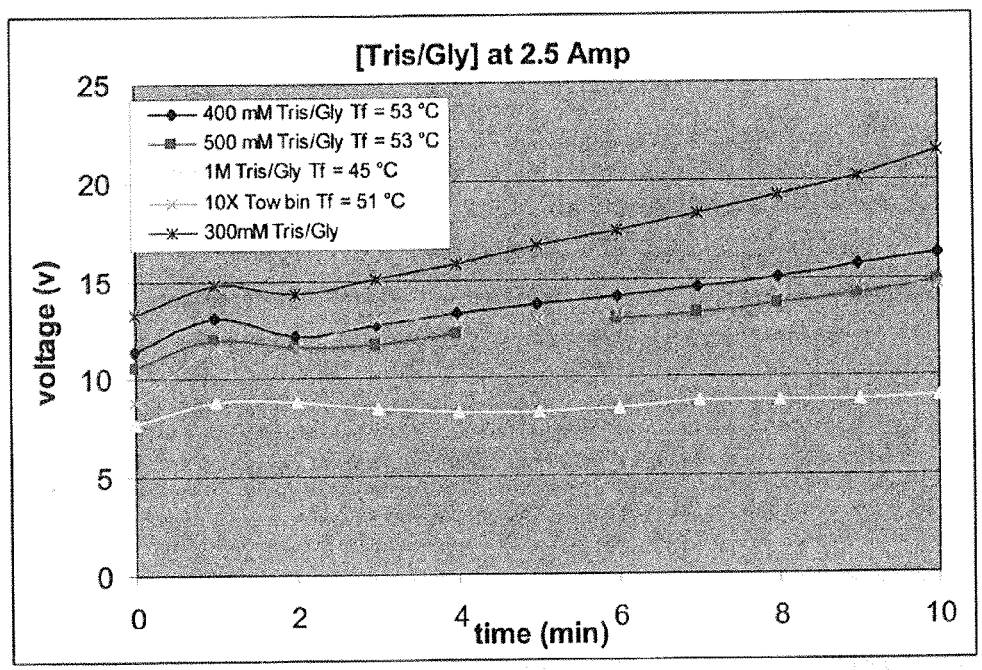
*Fig. 4* RSD Voltage during transfer

AQUEOUS TRANSFER BUFFER

CROSS-REFERENCES TO RELATED APPLICATIONS

This application is a continuation application of U.S. application Ser. No. 12/709,325, filed Feb. 19, 2010, now abandoned, which claims the benefit of U.S. Provisional Application No. 61/154,711, filed Feb. 23, 2009, the contents of all of which are hereby expressly incorporated by reference for all purposes.

BACKGROUND OF THE INVENTION

1. Field of Invention

This invention resides in the field of electrophoretic transfer of macromolecules, such as proteins and nucleic acids, and relates in particular to the transfer of polypeptide species from a matrix following electrophoresis, during which the polypeptide species were separated, to a second substrate for further detection and characterization.

2. Description of Prior Art

Electrophoresis is a fundamental tool in the modern laboratories of biological research. Typically, macromolecules such as proteins and nucleic acids become separated during electrophoresis as they migrate through a solid matrix in an electrical field. At the conclusion of an electrophoresis procedure, the macromolecules are found in distinct locations of the matrix depending on characteristics of the molecules such as molecular weight and electrical charge. Further studies of such macromolecules often require that the molecules be relocated to a second substrate where better reaction conditions are permitted. Electroblotting is one example of the post-electrophoresis transfer.

Numerous methods of electroblotting are well known and frequently practiced in the art. The transfer process is usually carried out in a liquid or semi-liquid environment where the macromolecules within an electrophoresis matrix, such as a polyacrylamide gel, is transferred to a second matrix suitable for further analysis, such as a membrane of nitrocellulose, nylon, etc. The movement of the macromolecules from the electrophoretic matrix to the analytical matrix is facilitated by an aqueous transfer buffer, which plays an important role in the efficiency of the transfer.

Various publications describe transfer buffers useful for the purpose of electroblotting, see, e.g., Towbin et al. (1979) *Proc. Natl. Acad. Sci. USA* 76:4350-4354; Timmons and Dunbar (1990) *Methods in Enzymology* 182:679-688. The present inventors provide a new aqueous transfer buffer that offers improved transfer efficiency, especially for polypeptides of relatively low molecular weight range.

BRIEF SUMMARY OF THE INVENTION

In one aspect, this invention relates to an aqueous buffer that is useful for eletrophoretic transfer of biomolecules, such as proteins and nucleic acids, from a matrix used in eletrophoresis to a second substrate appropriate for additional analysis. In general, the aqueous buffer of this invention contains Tris at a concentration of at least 300 mM and glycine at a concentration of at least 300 mM. In some embodiments, the buffer may further include ethanol or methanol at a concentration of no greater than 20% by weight. Or the buffer may further include a detergent, such as SDS, at a concentration of no greater than 0.1% by weight.

In some embodiments, the buffer contains Tris at a concentration of about 300 mM; or it may contain glycine at a concentration of about 300 mM. In some cases, the pH of the buffer is about 9.0. In particular example, the buffer has about 300 mM of Tris, about 300 mM of glycine, and a pH of about 9.0. In anther case, the concentration of Tris is about 400 mM, the concentration of glycine is about 400 mM, and the solution has a pH of about 9.0. One further example is a buffer having about 500 mM of Tris, about 500 mM of glycine, and a pH of about 9.0.

In other embodiments, the buffer of this invention contains at least one of Tris or glycine at a concentration of about 1 M or higher. For example, the buffer may contain Tris at about 1 M, glycine at about 1 M, and its pH is at about 9.0. As another example, the buffer contains about 250 mM of Tris, about 1.92 M of glycine, and has a pH of about 8.3.

In another aspect, this invention also relates to an electrophoretic transfer device containing the aqueous transfer buffer as described herein. In a further aspect, this invention relates to a method of electrophoretic transfer, which utilizes the aqueous transfer buffer described herein.

BRIEF DESCRIPTION OF THE DRAWINGS

FIG. 2 compares transfer efficiency of nine proteins using six different buffers as measured by SYPRO Ruby staining The following buffers were used:
400 mM Tris/Gly—400 mM Tris, 400 mM Glycine pH 9.0
500 mM Tris/Gly—500 mM Tris, 500 mM glycine pH 9.0
1M Tris/Gly—1,000 mM Tris, 1,000 mM glycine pH 9.0
10× Towbin—250 mM Tris, 1,920 mM glycine pH 8.3
300 mM Tris/Gly—300 mM Tris, 300 mM glycine pH 9.0
iBlot—proprietary consumables used, exact buffer composition unknown.

FIG. 3 shows the blots used for quantification depicted in FIG. 2.

FIG. 4 shows the voltage curve during transfer using six different transfer buffers.

DETAILED DESCRIPTION OF THE INVENTION

Figure 1A:
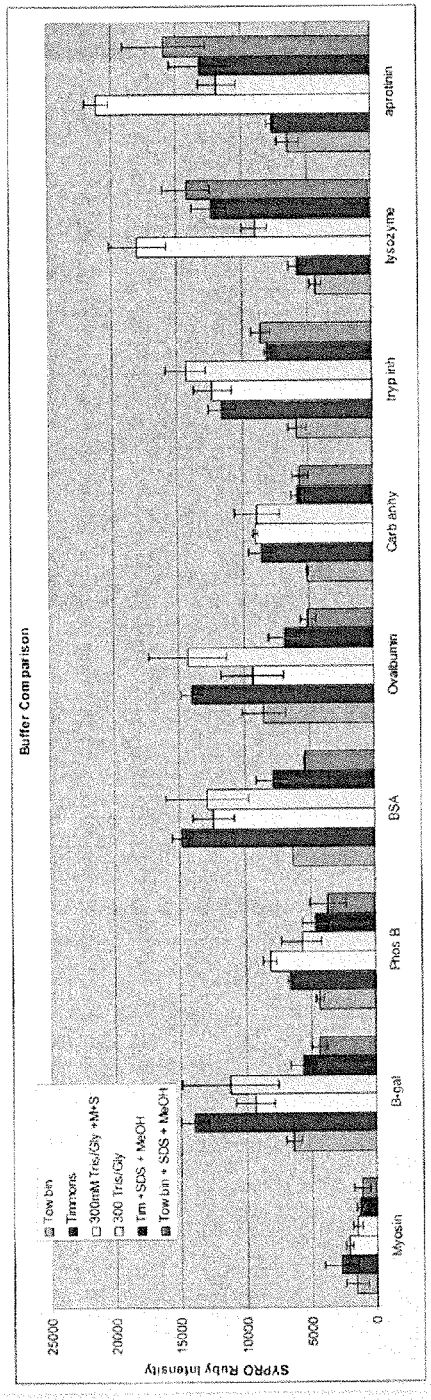
FIG. 1A compares the transfer efficiency of nine proteins using six different transfer buffers as measured by SYPRO Ruby intensity. Molecular weights of the proteins are as follows: Myosin—200 kDa; β-galactosidase—116 kDa; Phosphorylase B—97 kDa; Bovine Serum Albumin—66 kDa; Ovalbumin—45 kDa; Carbonic Anhydrase—31 kDa; Trypsin Inhibitor—21.5 kDa; Lysozyme—14.4 kDa; Aprotinin—6.5 kDa. The following buffers were used:
Towbin—25mM Tris, 192 mM Glycine, pH 8.3
Timmons—250 mM Tris, 192 mM Glycine, pH 8.9
300 mM Tris/Gly+M+S—300 mM Tris, 300 mM Glycine, 20% MeOH, 0.05% SDS pH 9.0
300 mM Tris/Gly—300mM Tris, 300 mM Glycine pH 9.0
Tim+SDS+MeOH—250 mM Tris, 192 mM Glycine, 20% MeOH, 0.05% SDS pH 8.9
Towbin+SDS+MeOH—25mM Tris, 192 mM Glycine, 20% MeOH, 0.05% SDS pH 8.3

This invention relates to an aqueous transfer buffer with improved performance in eletrophoretic transfer of macromolecules, including proteins and nucleic acids, especially proteins of relatively low molecular weight.

Ingredients of the Transfer Solution

The transfer buffer of this invention is an aqueous solution that contains at least two ingredients: Tris and glycine. Each of the two ingredients is present in the transfer solution at a concentration of at least 300 mM. In one example, a transfer buffer of this invention has a pH of 9.0 and contains 300 mM Tris and 300 mM glycine. Compared to the buffers in the art, this buffer has demonstrated a surprisingly high efficiency in transferring proteins across of a broad range of molecular weight (e.g., from about 200 kDa to about 6.5 kDa) from an electrophoretic gel to a blotting membrane, especially in the transfer of proteins of less than about 20 kDa. The concentrations of Tris and glycine can be higher in the solution (such as at least about 400 mM, 500 mM, or 1 M each), and may be as high as their respective solubility: 4 M for Tris and 3.3 M for glycine. In general, however, when the Tris and glycine concentrations in a transfer solution become increasingly higher than 300 mM each, the solution tends to retain its high transfer efficiency with regard to smaller proteins (e.g., about 20 kDa or less, about 15 kDa or less, about 20 kDa to about 6.5 kDa, or about 15 kDa to about 6.5 kDa), but may exhibit gradually diminished transfer efficiency of larger proteins (e.g., more than about 20 kDa or about 50 kDa).

Optionally, additional ingredients can be included in the transfer buffer as well. SDS, ethanol, and methanol are examples of such optional ingredients. In some examples, the concentration of SDS in the solution can range from 0.025% to 0.1% by weight, e.g., no more than 0.1% by weight, such as 0.05% by weight. In other examples, the concentration of ethanol or methanol in the solution can range from 5% to 20%, e.g., no more than 20% in weight, such as 10% by weight.

pH of the Transfer Solution

The transfer butter of this invention has a pH range of from about 8.0 to about 9.5, such as about 8.8 to about 9.2. In an exemplary embodiment, the transfer solution has a pH of about 9.0. As it is well known in the art, the solution's pH may be adjusted by diluted HCl or NaOH water solution as needed. As used in this application, the word "about" denotes a range of +/− 10% of the value indicated immediately after "about."

Method and Device Using the Transfer Solution

The transfer buffer of this invention can replace various transfer buffers currently used in the electrophoretic blotting methods known in the art and/or in combination with the devices currently available for electrophoretic blotting. In general, the process of electrophoretic blotting involves placing the matrix that was used in electrophoresis and contains the separated proteins in immediate contact with a second substrate to which the proteins are to be transferred for further testing. The matrix used in electrophoresis may be a polyacrylamide gel such as an SDS gel, and the second substrate may be a membrane made of nitrocellulose, nylon, polyvinyl difluoride, or similar material. The assembly of the matrix and substrate is submerged or saturated in the transfer buffer and then placed in an electrical field that directs the movement of proteins towards the second substrate. The voltage, current, and run time in a transfer system may be empirically determined. In some cases, it may be desirable to maintain the entire transfer assembly in a temperature-controlled environment to prevent overheating and possible protein denaturation.

EXAMPLES

The following examples are provided by way of illustration only and not by way of limitation. Those of skill in the art will readily recognize a variety of non-critical parameters that could be changed or modified to yield essentially the same or similar results.

Example 1

Effects of Tris/Glycine Concentrations on Protein Transfer Efficiency

Methods

A dilution series of SDS-PAGE Broad Range standards were separated by eletrophoresis on a Criterion 4-20% gel. Gels were blotted to 0.2 µM nitrocellulose membranes. To accommodate the low resistance values inherent in high ionic strength buffers, a custom power supply built by Acopian Technical Company was used. Current was set at 2.5 A and voltage data were recorded every minute. The blots were stained with SYPRO Ruby and imaged on a VersaDoc 4000.

In each case, blotting was performed for 10 minutes using EcoCloth pads (described in U.S. Ser. No. 11/955,955, "Polymeric Sorbent Sheets as Ion Reservoirs for Electroblotting"). For the experiment comparing Towbin Buffer, Timmons Buffer, and the buffer of this invention, voltage was held constant at 25V with a 2.5 A limit so that the transfer using Towbin Buffer would not overheat. For Timmons Buffer and the buffer of this invention, however, the 2.5 A limit was reached after less than 2 minutes and remained essentially the constant value for the remainder of the transfer. For the experiment comparing increasing concentrations of Tris/Glycine, current was held constant at 2.5 A.

Buffers Tested
1. 400 mM Tris, 400 mM Glycine, pH 9.0
2. 500 mM Tris, 500 mM Glycine, pH 9.0
3. 1 M Tris, 1 M Glycine, pH 9.0
4. 10× Towbin Buffer (250 mM Tris, 1.92 M Glycine), pH 8.3
5. 300 mM Tris, 300 mM Glycine, pH 9.0

Additional buffers are provided in the section of Brief Description of the Drawings.

Results

Blot Transfer Efficiency

Figure 1C:
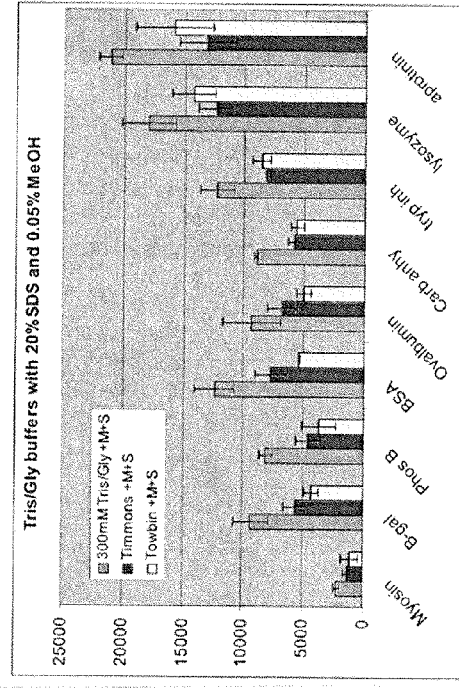
FIG. 1C compares the transfer efficiency of nine proteins using three different transfer buffers (further containing 20% methanol and 0.05% SDS) as measured by SYPRO Ruby intensity.
Figure 1B:
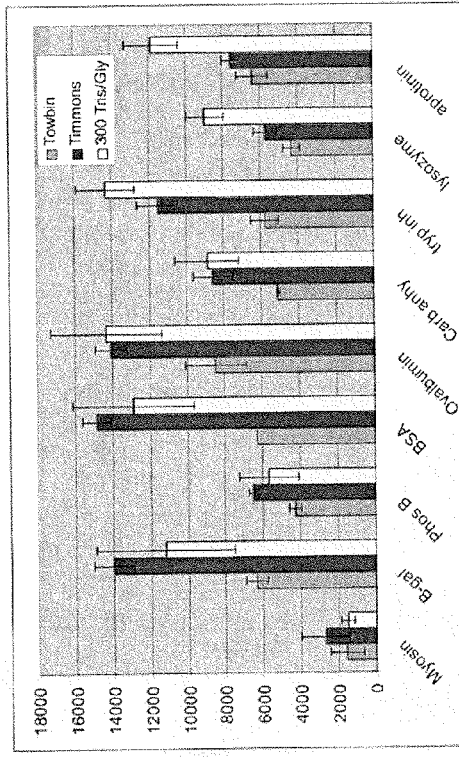
FIG. 1B compares the transfer efficiency of nine proteins using three different transfer buffers (containing Tris and glycine) as measured by SYPRO Ruby intensity.

FIGS. 1-4 compare SYPRO Ruby signal intensity from blots using various different buffer formulations. Overall, the concentration of Tris and Glycine in the buffer has a significant effect on transfer efficiency. Tris/Glycine concentrations above 300 mM decrease overall transfer efficiency for proteins larger than 14 kDa. In addition, the 1 M Tris/Glycine blot reveals an uneven transfer across the membrane (FIG. 5). For the two smallest proteins in the sample, lysozyme (14.4 kDa) and aprotinin (6.5 kDa), the two highest Tris/Glycine concentrations (1M and 10× Towbin, which contains 250 mM Tris and 1.92 M Glycine) display a significant increase in transfer efficiency. This suggests that a high ionic strength could help prevent migration of low molecular weight proteins through the membrane. However, the 500 mM Tris/Glycine buffer displays a low molecular weight transfer efficiency similar to that of 300 mM Tris/Glycine and 400 mM Tris/Glycine buffer have the poorest transfer efficiency.

Transfer Voltage

As expected, buffer concentration did have a large effect on the voltage profile generated during testing. In general, as the concentrations of Tris and Glycine increase, the voltage generated during the transfer decreases when current is held constant. Interestingly, the 1M Tris/Glycine held a significantly lower run voltage than the 10× Towbin (250 mM and 1.92 M Glycine), suggesting that Tris may have a more significant effect than Glycine on run voltage.

Conclusions

Increasing the Tris/Glycine concentration in the transfer buffer increases transfer efficiency for proteins of relatively small molecular weight, such as 20 kDa or smaller (e.g., 14 kDa or smaller). 1 M Tris/Glycine and 10× Towbin Buffer provide enhancement in small protein transfer efficiency, whereas the larger proteins tend to have relatively lower blotting quality and transfer efficiency.

All patents, patent applications, and other publications cited in this application are incorporated by reference in the entirety for all purposes.

What is claimed is:

1. A method for electrophoretic transfer comprising the step of transferring polypeptides of about 200 kDa to about 6.5 kDa in molecular weight from a first substrate to a second substrate in an electrical field after the first substrate and the second substrate are placed in an aqueous solution comprising Tris at a concentration of about 300 mM and glycine at a concentration of about 300 mM.

2. The method of claim 1, wherein the first substrate is a polyacrylamide gel and the second substrate is a membrane made of nylon, nitrocellulose, or polyvinyl difluoride.

3. The method of claim 1, wherein the polypeptides have been separated by electrophoresis in the first substrate prior to the transferring step.

4. The method of claim 1, wherein the polypeptides have a molecular weight of 20 kDa or less.

5. The method of claim 4, wherein the polypeptides have a molecular weight of 14 kDa or less.

6. The method of claim 1, wherein the transferring step is carried out at a constant voltage of 25 V.

7. The method of claim 1, wherein the transferring step is carried out at a constant amperage of 2.5 A.

8. The method of claim 1, wherein the solution further comprises ethanol or methanol at a concentration of no greater than 20% by weight.

9. The method of claim 1, wherein the solution further comprises a detergent at a concentration of no greater than 0.1% by weight.

10. The method of claim 9, wherein the detergent is SDS.

11. The method of claim 10, wherein the concentration of SDS is 0.05% by weight.

12. The method of claim 1, wherein the solution has a pH of about 9.0.

13. The method of claim 1, wherein the concentration of Tris is 300 mM, the concentration of glycine is 300 mM, and the solution has a pH of about 9.0.

14. The method of claim 1, wherein the solution has a pH of about 9.0 and further comprises methanol at a concentration of 20% by weight and SDS at a concentration of 0.05% by weight.

* * * * *